(12) United States Patent
Buendgen

(10) Patent No.: US 7,145,061 B1
(45) Date of Patent: Dec. 5, 2006

(54) INBRED CORN LINE G0603

(75) Inventor: Mike B. Buendgen, Madison, WI (US)

(73) Assignee: Syngenta (AT) Limited, Sleaford (GB)

( * ) Notice: Subject to any disclaimer, the term of this patent is extended or adjusted under 35 U.S.C. 154(b) by 0 days.

(21) Appl. No.: 10/377,963

(22) Filed: Feb. 28, 2003

(51) Int. Cl.
*C12N 15/82* (2006.01)
*A01H 5/00* (2006.01)
*A01H 5/10* (2006.01)
*A01H 1/00* (2006.01)

(52) U.S. Cl. .................. 800/320.1; 800/260; 800/265; 800/278; 800/298; 800/295; 800/279; 800/302; 435/412; 435/424; 435/430.1; 435/468

(58) Field of Classification Search ............ 800/320.1, 800/265, 298, 278, 295, 260, 279, 302; 435/412, 435/424, 430.1, 430, 421, 468
See application file for complete search history.

(56) References Cited

U.S. PATENT DOCUMENTS 5,523,520 A * 6/1996 Hunsperger et al. ........ 800/260
5,585,541 A 12/1996 Hable
5,973,239 A * 10/1999 Foley ..................... 800/320.1

OTHER PUBLICATIONS

Kraft et al. Theor. Appl. Genet., 2000, vol. 101, pp. 323-326.*
Eshed et al. Genetics, 1996, vol. 143, pp. 1807-1817.*
Conger, B.V., F.J. Novak, R. Afza, and K. Erdelsky. "Somatic embryogenesis from cultured leaf segments of Zea mays", Plant Cell Reports, 6:345-347 (1987).
Duncan, D.R., M.E. Williams, B.E. Zehr and J.M. Widholm. "The production of callus capable of plant regeneration from immature embryos of numerous Zea mays genotypes", Planta, 165:322-332 (1985).
Edallo, et al., "Chromosomal Variation and Frequency of Spontaneous Mutation Associated with in Vitro Culture and Plant Regeneration in Maize" Maydica XXXVI, pp. 39-56 (1981).
Forsberg, R.A. and R.R. Smith. "Sources, Maintenance, and Utilization of Parental Material", Hybridization of Crop Plants, Chapter 4, pp. 65-81 (1980).
Green, C.E. and R.L. Phillips. "Plant Regeneration from Tissue Cultures of Maize", Crop Science, vol. 15, pp. 417-421 (1975).
Green, C.E. and C.A. Rhodes. "Plant Regeneration in Tissue Cultures of Maize", Maize for Biological Research, pp. 367-372 (1982).
Hallauer, et al, "Corn Breeding", Corn and Corn Improvement pp. 463-564 (1988). Sprague et al, eds.
Meghji, M.R., J.W. Dudley, R.J. Lambert, and G.F. Sprague. "Inbreeding Depression, Inbred and Hybrid Grain Yields, and Other Traits of Maize Geotypes Representing Three Eras". Crop Science, vol. 24, pp. 545-549 (1984).
Phillips, et al., "Cell/Tissue Culture and IN Vitro Manipulation", In Corn & Corn Improvement, $3^{rd}$ Ed., ASA Publication, #18, pp. 345-349 & 356-357 (1988).
Poehlman, John Milton. Breeding Field Corp, AVI Publishing Company, Inc., Westport, Connecticut, pp. 237-246 (1987).
Sass (1977) "Morphology". In Corn & Corn Improvement. ASA Publication. Madison, WI, pp. 89-109.
Songstad, David D., David R. Duncan, and Jack M. Widholm. "Effect of 1-aminocyclopropane-1-carboxylic acid, silver nitrate, and norbornadiene on plant regeneration from maize callus cultures", Plant Cell Reports, 7:262-265 (1988).
M.P. Rolston. "Use of Endophyte in Plant Breeding and the Commercial Release of New Endophyte-Grass Associations". Proc. Of the second Int'l Symposium on Acremonium/Grass Interactions: Plenary Papers (pp. 171-174).
Tomes, et al, "the Effect of Parental Genotype on Initiation of Embryogenic Callus from Elite Maize (Zea mays 1.) Germplasm". Theor. Appl. Genet. 70., pp. 505-509. (1985).
Troyer, et al., "Selection for Early Flowering in Corn: 10 Late Synthetics". Crop Science, vol. 25, pp. 695-697 (1985).
Umbeck, et al. "Reversion of Male-Sterile T-Cytoplasm Maize to Male Fertility in Tissue Culture", Crop Science vol. 23, pp. 584-588 (1983).
Wright, H., "Commercial Hybrid Seed Production", Hybridization of Crop Plants, pp. 161-176, (1980).
Wych, R.D., "Production of Hybrid Seed Corn"; Corn and Corn Improvement, pp. 565-607 (1988).

* cited by examiner

*Primary Examiner*—Medina A. Ibrahim
(74) *Attorney, Agent, or Firm*—Dana S Rewoldt

(57) ABSTRACT

Broadly this invention provides an invention which is inbred corn line G0603. The methods for producing a corn plant by crossing the inbred line G0603 are also encompassed by the invention. Additionally, the invention relates to the various parts of inbred G0603 including culturable cells. This invention relates to hybrid corn seeds and plants produced by crossing the inbred line G0603 with at least one other corn line.

14 Claims, No Drawings

INBRED CORN LINE G0603

FIELD OF THE INVENTION

This invention is in the field of corn breeding, specifically relating to an inbred corn line designated G0603. This invention also is in the field of hybrid maize production employing the present inbred.

BACKGROUND OF THE INVENTION

The original maize plant was indigenous to the Western Hemisphere. The plants were weedlike and only through the efforts of early breeders were cultivated crop species developed. The crop cultivated by early breeders, like the crop today, could be wind pollinated. The physical traits of maize are such that wind pollination results in self-pollination or cross-pollination between plants. Each plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

The development of a planned breeding program for maize only occurred in the last century. A large part of the development of the maize product into a profitable agricultural crop was due to the work done by land grant colleges. Originally, maize was an open pollinated variety having heterogeneous genotypes. The maize farmer selected uniform ears from the yield of these genotypes and preserved them for planting the next season. The result was a field of maize plants that were segregating for a variety of traits. This type of maize selection led to, at most, incremental increases in seed yield.

Large increases in seed yield were due to the work done by land grant colleges that resulted in the development of numerous hybrid corn varieties in planned breeding programs. Hybrids were developed by selecting corn lines and selfing these lines for several generations to develop homozygous pure inbred lines. One selected inbred line was crossed with another selected inbred line to produce hybrid progeny (F1). The resulting hybrids, due to heterosis, are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogenity of the inbred maize lines is that all hybrid seed produced from any cross of two such elite lines will be the same hybrid seed and make the same hybrid plant. Thus the use of inbreds makes hybrid seed which can be reproduced readily. The hybrid plant in contrast does not produce hybrid seed that is readily reproducible. The seed on a hybrid plant is segregating for traits.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soil. Thus, a variety of major agronomic traits are important in hybrid combination for the various Corn Belt regions, and have an impact on hybrid performance.

Inbred line development and hybrid testing have been emphasized in the past half-century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, Hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating $F_1$ generation and self pollinating to produce a $F_2$ generation that segregates for traits and selecting progeny with the visual traits desired does not easily lead to a useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (corn Lethal necrosis and in the west soil that has excessively high pH levels. The industry often targets inbreds that address these issues specifically forming niche products. However, the aim of most large seed producers is to provide a number of traits to each inbred so that the corresponding hybrid can useful in a broader regions of the Corn Belt. The new biotechnology techniques such as Microsatellites, RFLPs, RAPDs and the like have provided breeders with additional tools to accomplish these goals.

SUMMARY OF THE INVENTION

The present invention relates to an inbred corn line G0603. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line G0603.

Generally then, broadly the present invention includes an inbred corn seed designated G0603. This seed produces a corn plant.

The invention also includes the tissue culture of regenerable cells of G0603 wherein the cells of the tissue culture regenerates plants capable of expressing the genotype of G0603. The tissue culture is selected from the group consisting of leaves, pollen, embryos, roots, root tips, guard cells, ovule, seeds, anthers, silk, flowers, kernels, ears, cobs, husks and stalks, cells and protoplasts thereof. The corn plant regenerated from G0603 or any part thereof is included in the present invention. The present invention includes regenerated corn plants that are capable of expressing G0603's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines G0603 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G0603 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G0603; cultivating corn plants resulting from said planting; permitting pollen from another inbred line to cross pollinate inbred line G0603; harvesting seeds produced on plants of the inbred; and growing a harvested seed are part of the method of this invention.

Likewise included is a first generation (F1) hybrid corn plant produced by the process of planting seeds of corn inbred line G0603; cultivating corn plants resulting from said planting; permitting pollen from inbred line G0603 to cross pollinate another inbred line; harvesting seeds produced on plants of the inbred; and growing a plant from such a harvested seed.

The inbred corn line G0603 and at least one transgenic gene adapted to give G0603 additional and/or altered phenotypic traits are within the scope of the invention. Such transgenes are usually associated with regulatory elements (promoters, enhancers, terminators and the like). Presently, trangenes provide the invention with traits such as insect resistance, herbicide resistance, disease resistance increased or deceased starch or sugars or oils, increased or decreased life cycle or other altered trait.

The present invention includes inbred corn line G0603 and at least one transgenic gene adapted to give G0603 modified starch traits. Furthermore this invention includes the inbred corn line G0603 and at least one mutant gene adapted to give modified starch, acid or oil traits. The present invention includes the inbred corn line G0603 and at least one transgenic gene selected from the group consisting of: *bacillus thuringiensis*, the bar or pat gene encoding Phosphinothricin acetyl Transferase, Gdha gene, EPSP synthase gene, low phytic acid producing gene, and zein. The inbred corn line G0603 and at least one transgenic gene useful as a selectable marker or a screenable marker are covered by the present invention.

A tissue culture of the regenerable cells of hybrid plants produced with use of G0603 genetic material is covered by this invention. A tissue culture of the regenerable cells of the corn plant produced by the method described above are also included.

DEFINITIONS

In the description and examples, which follow, a number of terms are used. In order to provide a clear and consistent understanding of the specifications and claims, including the scope to be given such terms, the following definitions are provided.

BL Moist

The moisture percentage of the grain at black layer, i.e., when 50%/o of the plants per plot have reached physiological maturity.

Cold Germ

Cold Germ is a measurement of seed germination under cold soil conditions. Data is reported as percent of seed germinating.

ECB

European corn borer is a maize eating insect. ECBI is the first brood generation of European corn borers. ECBII is the second generation of European corn borers. ECB1 is a rating of leaf damage. The ECBII (ECB2) rating is based upon tunneling. For all Entomology ratings, the higher number is best (1=little or no resistance, 9=highly resistant). The scale is slightly different for Ear Rating, which is taken on a 1–4 basis. This is a rating of corn borer feeding on the ear. A 1 represents feeding over the entire ear, while a 4 represents no observable feeding on the ear.

Emerge (EMG)

The number of emerged plants per plot (planted at the same seedling rate) collected when plants have two fully developed leaves.

GI

This is a selection index that provides a single quantitative measure of the worth of a hybrid based on four traits. FI is a very similar index which weights yield less than GI. In GI yield is the primary trait contributing to index values. The GI value is calculated by combining stalk lodging, root lodging, yield and dropped ears according to the attached mathematical formula:

$$GI=100+0.5(YLD)-0.9(\% \text{ STALK LODGE})-0.9(\% \text{ ROOT LODGE})-2.7(\% \text{ DROPPED EAR})$$

GLS

Gray Leaf Spot (*Cercospora Zeae*) disease rating. This is rated on a 1–9 scale with a "1" being very susceptible, and a "9" being very resistant.*

GW

Gross' Wilt (*Corynebacterium nebraskense*). This is rated on a 1–9 scale with a "1" being very susceptible, and a "9" being very resistant.*

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(\text{Max Temp (° F.)} + \text{Min Temp (° F.)})}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain that has reached physiological maturity (black layer).

HEATPEEK

The number of GDU's after planting of an inbred when approximately 50 percent of the plants show visible tassel extension.

HEATP50 or HTP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The corn is rated on a 1–9 scale with a "1" being very susceptible, and a "9" being very resistant.*

$MDMV_B$

Maize Dwarf Mosaic Virus strain B. This is rated on a 1–9 scale with a "1" being very susceptible and a "9" being very resistant.*

Moisture

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

PCT Tiller or Tiller Rating

The total number of tillers per plot divided by the total number of plants per plot.

Plant

This term includes the entire plant and its plant cells, plant protoplasts made from its cells, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like, and this term also includes any mutated gene, transgenic DNA or (RNA) or portion thereof that have been introduced into the plant by whatever method.

Plant Height (PLTHT) (PHT)

The distance in centimeters from ground level to the base of the tassel peduncle.

Plant Integrity (PLTINT) or (INT)

The level of plant integrity on a scale of 1–9 with 9 evidencing the trait most strongly: 1–2.9 ratings are low plant integrity, 3–5.9 ratings are intermediate plant integrity, and 6–9 ratings are strongly evidencing plant integrity.

Population (POP)

The plant population.

RM

Predicted relative maturity based on the moisture percentage of the grain at harvest. This rating is based on known set of checks and utilizes standard linear regression analyses and is referred to as the Minnesota Relative Maturity Rating System.

Shed

The volume of pollen shed by the male flower rated on a 1–5 scale where a "1" is a very light pollen shedder, a "2.5" is a moderate shedder, and a "5" is a very heavy shedder.

SLB

Southern Leaf Blight (*Bipolaris maydis*) disease rating. This is rated on a 1–9 scale with a "1" being very susceptible, and a "9" being very resistant.*

Staygreen (SGN)

The level of staygreen of the plant on a scale of 1–9 with 9 evidencing the trait most strongly: 1–2.9 ratings are low staygreen, 3–5.9 ratings are intermediate staygreen, and 6–9 ratings are strongly evidencing staygreen.

TWT

The measure of the weight of grain in pounds for a one bushel volume adjusted for percent grain moisture.

Vigor (VIG)

Visual rating of 1 to 9 made 2–3 weeks post-emergence where a "1" indicates very poor early plant development, and a "9" indicates superior plant development.

Warm Germ

A measurement of seed germination under ideal (warm, moist) conditions. Data is reported as percent of seeds germinating.

Yield (YLD)

Actual yield of grain at harvest adjusted to 15.5% moisture. Measurements are reported in bushels per acre.

% Dropped Ears (DE)

The number of plants per plot, which dropped their primary ear, divided by the total number of plants per plot.

% Root Lodge (RL)

Percentage of plants per plot leaning more that 30 degrees from vertical divided by total plants per plot.

% Stalk Lodge (SL)

Percentage of plants per plot with the stalk broken below the primary ear node divided by the total plants per plot.

% Cull

Percentage of seed that passes through a $16/64$ inch screen or will not pass through a $25/64$ inch screen.

*Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

G0603 Is a vigorous plant with a big leaf, and large tassels which shed pollen well.

The line works well as either a female or as a male. This line has girthy ears that are well filled. G0603 shows excellent germination in both cold and warm conditions.

The inbred has shown uniformity and stability within the limits of environmental influence for all the traits as described in the Variety Description Information (Table 1) that follows.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G0603.

The best method of producing the invention, G0603 which is substantially homozygous, is by planting the seed of G0603 which is substantially homozygous and self-pollinating or sib pollinating the resultant plant in an isolated environment, and harvesting the resultant seed.

TABLE 1

G0603
VARIETY DESCRIPTION INFORMATION

| | | |
|---|---|---|
| #1 | Type: Dent | |
| #2 | Region Best Adapted: Broadly adapted-northwestern regions of the Corn Belt. This inbred in hybrid combination usually has RM of about 99–100 days. | |
| #3 | Plant Traits | |
| | Plant Height | 59 in. |
| | Ear Height | 23 in. |
| | Tillers (Rating) | 5 |
| | Leaf Color | GREEN |
| | Silk Color | Yellow |
| #4 | Tassel Traits | |
| | Glume Ring Color | OTHER/ABSENT |
| | Anther Color | Other |
| #5 | Ear and Kernel Traits | |
| | Cob Color | RED |
| | Kernel Crown Color | YELLOW |
| #6 | Disease Resistance In Inbred | |
| | | Eye Spot = 6.6 |
| | | Gross' Wilt = 4.4 |
| | | Northern Leaf Blight = 5.2 |
| #7 | Insect Resistance In Inbred | |
| | | ECB1 = 4.8 |
| | | ECB2 = 2.7 |
| | | Ear rate = 2.3 |
| #8 | The comparable inbred to G0603 is ZS1513 as described in U.S. Pat. No. 5,585,541. ZS1513 has a number of similarities to the present invention. ZS1513 is an inbred which has been or is presently in a number of commercial hybrids that are in a similar region of adaptation as most of the hybrids formed with G0603. | |

The data provided above is often a color. The Munsell code is a reference book of color, which is known and used in the industry and by persons with ordinary skill in the art of plant breeding.

The purity and homozygosity of inbred G0603 is constantly being tracked using isozyme genotypes as shown in Table 2.

Isozyme Genotypes for G0603

Isozyme data were generated for inbred corn line G0603 according to procedures known and published in the art. The data in Table 2 gives the electrophoresis data on G0603 as compared to its two parents.

TABLE 2

ELECTROPHORESIS RESULTS FOR G0603

| INBRED | ACP1 | ACP4 | ADH | MDH1 | MDH2 | PGD1 | PGD2 | PHI | PGM | IDH |
|---|---|---|---|---|---|---|---|---|---|---|
| G0603 | 11 | 00 | 22 | 11 | 11 | 11 | 11 | 22 | 22 | 22 |
| Parent 1 | 11 | 00 | 22 | 11 | 11 | 11 | 11 | 22 | 22 | 11 |
| Parent 2 | 11 | 00 | 22 | 22 | 11 | 11 | 11 | 22 | 22 | 22 |

Inbred and Hybrid Performance of G0603

The traits and characteristics of inbred corn line G0603 are listed to compare with other inbreds and/or in hybrid combinations. The G0603 data shows the characteristics and traits of importance, giving a snapshot of G0603 in these specific environments.

Table 3A shows a comparison between G0603 and a comparable inbred ZS1513. G0603 has significantly better cold germination than does inbred ZS1513. The two inbreds show significant differences in plant height, and across all Heat measurements for silking. G0603 has comparable yield at harvest as does ZS1513 but has similar moisture at harvest. G0603 has significantly less large medium flat and plateless seeds than does ZS1513.

PAIRED INBRED COMPARISON DATA

| Year | Inbred | Yield | Moisture | Ear Height | Plant Height | Emerge | Heat Peek | Heat Peek | Heatp10 | Heatp50 | Heatp90 | Heats10 | Heats50 |
|---|---|---|---|---|---|---|---|---|---|---|---|---|---|
| Overall | G0603 | 72.9 | 11.3 | 59.1 | 153.4 | 91.4 | 1330.9 | 1330.9 | 1366.3 | 1395.8 | 1569.6 | 1400.3 | 1447.6 |
|  | ZS1513 | 82.9 | 11.5 | 61.6 | 140.0 | 83.1 | 1324.2 | 1324.2 | 1366.7 | 1399.5 | 1569.6 | 1388.3 | 1422.4 |
|  | # Expts | 4.0 | 4.0 | 4.0 | 4.0 | 4.0 | 4.0 | 4.0 | 4.0 | 4.0 | 4.0 | 4.0 | 4.0 |
|  | Diff | 10.0 | 0.2 | 2.5 | 13.3 | 8.3 | 6.7 | 6.7 | 0.3 | 3.7 | 0.0 | 12.0 | 25.1 |
|  | Prob | 0.1 | 0.8 | 0.6 | 0.034** | 0.1 | 0.4 | 0.4 | 1.0 | 0.4 | 1.0 | 0.041** | 0.073* |

| | Year | Inbred | Heats90 | % Lrg Med Flat | % Lrg Med Rnd | % Lrg Plateless | % Sml Med Flat | % Sml Med Rnd | % Sml Plateless | Shed | Cold Germ | Warm Germ |
|---|---|---|---|---|---|---|---|---|---|---|---|---|
| | Overall | G0603 | 1497.1 | 19.1 | 17.1 | 1.7 | 16.1 | 32.6 | 9.3 | 4.3 | 95.6 | 97.8 |
| |  | ZS1513 | 1465.1 | 39.9 | 19.4 | 12.9 | 10.4 | 11.7 | 3.0 | 3.8 | 89.4 | 96.2 |
| |  | # Expts | 4.0 | 4.0 | 4.0 | 4.0 | 4.0 | 4.0 | 4.0 | 4.0 | 4.0 | 4.0 |
| |  | Diff | 31.9 | 20.9 | 2.3 | 11.2 | 5.7 | 20.9 | 6.4 | 0.5 | 6.3 | 1.6 |
| |  | Prob | 0.068* | 0.006*** | 0.5 | 0.047** | 0.023** | 0.005*** | 0.008*** | 0.4 | 0.001*** | 0.4 |

TABLE 3B

PAIRED HYBRID COMPARISON DATA

| Year | Hybrid | Yield | FI | GI | Y_M | Moisture | % Root Lodge | % Stalk Lodge | % Drop Ear | Test Weight |
|---|---|---|---|---|---|---|---|---|---|---|
| Overall | G0603/CI* | 164.7 | 124.9 | 175.6 | 7.8 | 22.0 | 2.8 | 3.9 | 0.4 | 55.1 |
|  | Commercial Hybrid (having CI*) | 157.3 | 125.6 | 174.1 | 7.8 | 21.1 | 2.6 | 2.0 | 0.2 | 54.7 |
|  | # Expts | 132.0 | 130.0 | 130.0 | 132.0 | 132.0 | 130.0 | 130.0 | 130.0 | 130.0 |
|  | Diff | 7.5 | 0.7 | 1.5 | 0.0 | 1.0 | 0.2 | 1.9 | 0.2 | 0.4 |
|  | Prob | 0.000*** | 0.5 | 0.2 | 0.6 | 0.000*** | 0.8 | 0.000*** | 0.008*** | 0.000*** |

\*.05 < Prob <= .10
\*\*.01 < Prob <= .05
\*\*\*.00 < Prob <= .01
*CI = common inbred to each hybrid Table 3B shows the Inbred G0603 in hybrid combination in comparison with another hybrid combination that is adapted to the same region. When in this hybrid combination the present inbred carries a significantly heavier test weight and a distinctively significant increase in yield and moisture levels into the hybrid. The Y/M for the hybrid combination containing the present invention is similar with the compared hybrid, although the compared hybrid has significantly lower moisture at harvest.

Table 4 shows the GCA (general combining ability) estimates of G0603 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids, particularly the leader in the industry and Garst Seed's commercial products and pre-commercial hybrids, which were grown in the same sets and locations. This Table shows that 138 crosses were analyzed. Each of these crosses were made in small plots with not less than 50 hybrid seeds being planted per cross. These experiments produced progeny of G0603 by a number of different lines. The grain produced by these hybrids have the present invention as an ancestor. The hybrid grain would be genetically different from the hybrid seed that formed the plant on which the hybrid grain was produced. However, such grain would be readily identifiable as being progeny of the invention or as having the invention as an ancestor.

TABLE 4

G0603

| One parent in each hybrid tested to provide this data is G0603 | N99 | N00 | N01 | N | FI | Y_M | GI | YLD | MST | % SL | % RL | % DE | TWT | POP | RM |
|---|---|---|---|---|---|---|---|---|---|---|---|---|---|---|---|
| XR = | 4 | 16 | 117 | 138 | −2.0 | −0.2 | −0.1 | 0.7 | −0.8 | −2.4 | 2.2 | 0.0 | 0.3 | 189.0 | 100.0 |
| XH = | 4 | 16 | 117 | 19 | −4.9 | −0.4 | −2.9 | −3.2 | −0.9 | −3.8 | 2.5 | 0.0 | −0.1 | 245.0 | 100.0 |
| XT = | 4 | 16 | 117 | 3 | 0.2 | −0.1 | 1.0 | 0.9 | −0.4 | −1.9 | 3.1 | −0.1 | 0.6 | 217.0 | 98.0 |

XR = GCA
Estimate: Weighted by experiment
XH = GCA
Estimate: Weighted by Parent 2
XT = Same as XH but using only those parent 2 with two years of data
FI = 100 + 0.5 (Yld) − 2.3(MST) − 0.9(% SL) − 0.9(% RL) − 2.7(% DE)
POP = plants per acre
RM = The Minnesota Relative Maturity Table 4 shows G0603 in XR crossed to 19 different inbreds to form hybrid combinations. G0603 in hybrid combination shows an excellent advantage for yield and heavier test weight compared to the commercial checks and the company's other inbreds in hybrid combination. G0603 has a very positive rating for resistance to root lodging. Additionally when looking at XT the present inventions is carrying even more yield advantage, more test weight advantage and less moisture disadvantage than in XR.

TABLE 5A

YIELD RESPONSE
Research Plots

| HYBRID | YIELD | | | | | |
|---|---|---|---|---|---|---|
| G0603/CI* hybrid | 81 | 105 | 129 | 154 | 178 | 202 |
| Environment | 75 | 100 | 125 | 150 | 175 | 200 |

Error: 14.
Plots 170

TABLE 5B

YIELD RESPONSE
Research Plots

| HYBRID (having CI*) | YIELD | | | | | |
|---|---|---|---|---|---|---|
| Comparison hybrid | 84 | 105 | 126 | 147 | 168 | 189 |
| Environment | 75 | 100 | 125 | 150 | 175 | 200 |

Error: 12.2
Plots 2958

Table 5A shows the yield response of G0603 in hybrid combination in comparison with the plants in the environment around it at the same location. The data for the present inbred is showing consistently similar results in comparison to the environment level. G0603 in hybrid combination, is a workhorse inbred that works well by providing yields that compare to the environment yields regardless of yield potential of that environment. Table 5B shows the data from a different comparison hybrid. This comparison hybrid is not yielding particularly well in the high and mid environments. The comparison hybrid is not carrying the yield potential into the hybrid as well as the hybrid combination of the present invention.

backcrosses, hybrid production, crosses to populations, haploid by such old and known methods of using stock material that induces haploids and anther culturing and the like.

All plants and plant cells produced using inbred corn line G0603 are within the scope of this invention. The invention encompasses the inbred corn line used in crosses with other, different, corn inbreds to produce (F1) corn hybrid seeds and hybrid plants and the grain produced on the hybrid plant. This invention includes plant and plant cells, which upon growth and differentiation produce corn plants having the physiological and morphological characteristics of the inbred line G0603.

TABLE 6

Agronomic Traits
G0603/CI* vs commercial hybrid with IT (and CI*)

| YEAR | # | Early Stand | Adv | Emg | Adv | Vigor | Adv | S50 | Adv | P50 |
|---|---|---|---|---|---|---|---|---|---|---|
| YR 1 G0603/CI* | 10 | 76.8 | −5.4 | 4.5 | −0.2 | 5.4 | −0.4 | 83.0 | 1.0 | 83.0 |
| COMM.HYBRID IT | 10 | 82.1 | | 4.7 | | 5.7 | | 82.0 | | 82.0 |
| YR 2 G0603/CI* | 23 | 84.3 | 2.1 | 6.2 | 0.7 | 7.4 | 0.6 | 77.0 | 0.0 | 79.0 |
| COMM.HYBRID IT | 23 | 82.1 | | 5.5 | | 6.9 | | 77.0 | | 78.0 |
| YR 1 & 2 G0603/CI* | 33 | 82.4 | 0.2 | 5.5 | 0.3 | 6.7 | 0.2 | 78.0 | 0.0 | 80.0 |
| COMM.HYBRID IT | 33 | 82.1 | | 5.2 | | 6.5 | | 78.0 | | 79.0 |

| YEAR | # | Ear Ht. | Adv | Plant Ht. | Adv | Stay Green | Adv | Black Layer | Adv | Plant Int | Adv |
|---|---|---|---|---|---|---|---|---|---|---|---|
| YR 1 G0603/CI* | 10 | 38.4 | −0.6 | 84.8 | 1.3 | 6.0 | 1.0 | 149.0 | 2.0 | | |
| COMM.HYBRID IT | 10 | 39.0 | | 83.5 | | 5.0 | | 147.0 | | | |
| YR 2 G0603/CI* | 23 | 41.5 | −1.1 | 83.6 | 3.9 | 4.8 | 0.8 | 141.0 | 1.0 | 5.3 | −0.8 |
| COMM.HYBRID IT | 23 | 42.6 | | 79.6 | | 4.0 | | 141.0 | | 6.1 | |
| YR 1 & 2 G0603/CI* | 33 | 40.5 | −0.9 | 84.0 | 3.0 | 5.2 | 0.8 | 144.0 | 1.0 | 5.3 | −0.8 |
| COMM.HYBRID IT | 33 | 41.4 | | 80.9 | | 4.3 | | 143.0 | | 6.1 | |

*CI = common inbred to each hybrid
ADV = ADVANTAGE
IT = Imidazolinone herbicide resistance The data in show the Agronomic traits of the present inbred when in hybrid combination. The Table also shows a herbicide resistant commercial hybrid that has an inbred in common with the hybrid that includes the present invention. The first to rows of data show the Year one data the next two rows show the year 2 data and the last two rows shows the combined data of years 1 and 2. The environment in year one led to some lesser advantages being shown by the present inbred when in hybrid combination. However, in year 2 the hybrid containing G0603 thrived. The present invention in hybrid combination is carrying an overall advantage in early stand and in vigor and emergence. Additionally the present inbred when in hybrid combination is excellent stay green characteristics.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line G0603. Further, both first and second parent corn plants can come from the inbred corn line G0603 which produces a self of the inbred invention. The present invention can be employed in a variety of breeding methods which can be selected depending on the mode of reproduction, the trait, and the condition of the germplasm. Thus, any breeding methods using the inbred corn line G0603 are part of this invention: selfing, Additionally, this maize can, within the scope of the invention, contain: a mutant gene such as, but not limited to, the sugary 1 or shrunken 1 or waxy or AE or imazethapyr tolerant (IT or IR™) mutant gene; or transgenic genes such as but not limited to insect resistant genes such as Corn Rootworm gene, Bacillus thuringiensis (Cry genes), or herbicide resistant genes such as Pat gene or Bar gene, EPSP, or disease resistant genes such as the Mosaic virus resistant gene, etc., or trait altering genes such as flowering genes, oil modifying genes, senescence genes and the like. The methods and techniques for inserting or producing and/or identifying a mutation or a transgene into the present invention through breeding, transformation, or mutating are well known and understood by those of ordinary skill in the art.

Various techniques for breeding and moving or altering genetic material within or into the present invention (whether it is an inbred or in hybrid combination) are also known to those skilled in the art. These techniques to list only a few are anther culturing, haploid production, (stock six is a method that has been in use for thirty years and is well known to those with skill in the art), transformation, irradiation to produce mutations, chemical or biological mutation agents and a host of other methods are within the scope of the invention. All parts of the G0603 plant including its plant cells produced using the inbred corn line are within the scope of this invention. The term transgenic plant refers to plants having genetic sequences, which are introduced into the genome of a plant by a transformation method and the progeny thereof. Transformation methods are means for integrating new genetic coding sequences into the plant's genome by the incorporation of these sequences into a plant through man's assistance, but not by breeding practices. The transgene once introduced into plant material and integrated stably can be moved into other germplasm by standard breeding practices.

Though there are a large number of known methods to transform plants, certain types of plants are more amenable to transformation than are others. Transformation of dicots is usually achievable for example, tobacco is a readily transformable plant. Monocots can present some transformation challenges, however, the basic steps of transforming monocots have been known in the art for about 15 years. The most common method of maize transformation is referred to as gunning or microprojectile bombardment though other methods can be used. The process employs small gold-coated particles coated with DNA which are shot into the transformable material. Detailed techniques for gunning DNA into cells, tissue, callus, embryos, and the like are well known in the prior art. One example of steps that can be involved in monocot transformation are concisely outlined in U.S. Pat. No. 5,484,956 "Fertile Transgenic *Zea mays* Plants Comprising Heterologous DNA Encoding *Bacillus Thuringiensis* Endotoxin" issued Jan. 16, 1996 and also in U.S. Pat. No. 5,489,520 "Process of Producing Fertile *Zea mays* Plants and Progeny Comprising a Gene Encoding Phosphinothricin Acetyl Transferase" issued Feb. 6, 1996.

Plant cells such as maize can be transformed not only by the use of a gunning device but also by a number of different techniques. Some of these techniques include maize pollen transformation (See University of Toledo 1993 U.S. Pat. No. 5,177,010); Whiskers technology (See U.S. Pat. Nos. 5,464,765 and 5,302,523); electroporation; PEG on Maize; *Agrobacterium* (See 1996 article on transformation of maize cells in *Nature Biotechnology*, Volume 14, June 1996) along with numerous other methods which may have slightly lower efficiency rates. Some of these methods require specific types of cells and other methods can be practiced on any number of cell types.

The use of pollen, cotyledons, zygotic embryos, meristems and ovum as the target issue can eliminate the need for extensive tissue culture work. Generally, cells derived from meristematic tissue are useful. The method of transformation of meristematic cells of cereal is taught in the PCT application WO96/04392. Any number of various cell lines, tissues, calli and plant parts can and have been transformed by those having knowledge in the art. Methods of preparing callus or protoplasts from various plants are well known in the art and specific methods are detailed in patents and references used by those skilled in the art. Cultures can be initiated from most of the above-identified tissue. The only true requirement of the transforming plant material is that it can form a transformed plant.

The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used. The transgenic gene can come from various non-plant genes (such as; bacteria, yeast, animals, and viruses) along with being from plants.

The regulatory promoters employed can be constitutive such as CaMv35S (usually for dicots) and polyubiquitin for monocots or tissue specific promoters such as CAB promoters, MR7 described in U.S. Pat. No. 5,837,848, etc. The prior art promoters, includes but is not limited to, octopine synthase, nopaline synthase, CaMv19S, mannopine synthase. These regulatory sequences can be combined with introns, terminators, enhancers, leader sequences and the like in the material used for transformation.

The isolated DNA is then transformed into the plant. After the transformation of the plant material is complete, the next step is identifying the cells or material, which has been transformed. In some cases, a screenable marker is employed such as the beta-glucuronidase gene of the uidA locus of *E. coli*. Then, the transformed cells expressing the colored protein are selected. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular maize material are well known in the art.

A deposit of at least 2500 seeds of this invention will be maintained by Garst Seed Company, 2369 330th Street, Slater, Iowa 50244. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The date of deposit was Jun. 15, 2006. The ATCC number of the deposit is PTA-7656 and Jul. 17, 2006 the deposit was found viable when tested. The deposit of at least 2500 seeds will be from the same inbred seed taken from the deposit maintained by Garst Seed Company. The ATCC deposit will be maintained in that depository, which is a public depository, for a period of 30 years, or 5 years after the last request, or for the effective life of the patent, whichever is longer, and will be replaced if it becomes nonviable during that period.

Additional public information on some ZS designations may be available from the PVP Office, a division of the US Government.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. Seed of inbred corn line designated G0603, representative seed of said line having been deposited under ATCC accession number PTA-7656.

2. A corn plant produced by growing the seed of claim 1.

3. A tissue culture of regenerable cells produced from the corn plant of claim 2.

4. The tissue culture according to claim 3, wherein the regenerable cells are from plant parts selected from the group consisting of leaves, pollen, embryos, roots, root tips, meristem, ovule, anthers, silk, flowers, kernels, ears, cobs, husks and stalks.

5. A corn plant regenerated from the tissue culture of claim 3, wherein the regenerated plant has all of the physiological and morphological characteristics of G0603, representative seed of said line having been deposited under ATCC accession number PTA-7656.

6. A method of producing hybrid seed comprising crossing the corn plant of claim 2 with another different corn plant, and harvesting the resultant seed.

7. A method of producing a hybrid corn plant comprising crossing the corn plant of claim 2 with another different corn plant, harvesting the resultant seed, and growing a hybrid corn plant from said seed.

8. Pollen of the corn plant of claim 2.

9. A method of producing an herbicide resistant corn plant comprising introducing into the corn plant of claim 2 a transgene that confers herbicide resistance.

10. An herbicide resistant corn plant produced by the method of claim 9.

11. A method of producing an insect resistant corn plant comprising introducing into the corn plant of claim 2 a transgene that confers insect resistance.

12. An insect resistant corn plant produced by the method of claim 11.

13. A method of producing a disease resistant corn plant comprising introducing into the corn plant of claim 2 a transgene that confers disease resistance.

14. A disease resistant corn plant produced by the method of claim 13.

* * * * *